(12) United States Patent
Wang et al.

(10) Patent No.: US 12,165,748 B2
(45) Date of Patent: Dec. 10, 2024

(54) METHOD FOR IDENTIFYING KEY MODULE OR KEY NODE IN BIOMOLECULAR NETWORK

(71) Applicants: Zhong Wang, Beijing (CN); Yingying Zhang, Beijing (CN)

(72) Inventors: Zhong Wang, Beijing (CN); Yingying Zhang, Beijing (CN); Yongyan Wang, Beijing (CN)

(73) Assignees: Zhong Wang, Beijing (CN); Yingying Zhang, Beijing (CN)

( * ) Notice: Subject to any disclaimer, the term of this patent is extended or adjusted under 35 U.S.C. 154(b) by 979 days.

(21) Appl. No.: 16/096,276

(22) PCT Filed: Jan. 16, 2017

(86) PCT No.: PCT/CN2017/071209
§ 371 (c)(1),
(2) Date: Oct. 24, 2018

(87) PCT Pub. No.: WO2017/185834
PCT Pub. Date: Nov. 2, 2017

(65) Prior Publication Data
US 2019/0139621 A1 May 9, 2019

(30) Foreign Application Priority Data
Apr. 27, 2016 (CN) .......................... 201610269466.0

(51) Int. Cl.
*G16B 5/00* (2019.01)
*G16B 10/00* (2019.01)
*G16B 20/00* (2019.01)
*G16B 40/20* (2019.01)
*G16B 45/00* (2019.01)

(52) U.S. Cl.
CPC .............. *G16B 5/00* (2019.02); *G16B 10/00* (2019.02); *G16B 20/00* (2019.02); *G16B 40/20* (2019.02); *G16B 45/00* (2019.02)

(58) Field of Classification Search
None
See application file for complete search history.

(56) References Cited

PUBLICATIONS

"Centrality," Wikipedia, downloaded Oct. 1, 2022 from: https://en.wikipedia.org/wiki/Centrality, 12 pages, (2022).*
"Eigenvector centrality," Wikipedia, downloaded Oct. 1, 2022 from: https://en.wikipedia.org/wiki/Eigenvector_centrality, 3 pages, (2022).*
"Betweenness centrality," Wikipedia, downloaded Oct. 1, 2022 from: https://en.wikipedia.org/wiki/Betweenness_centrality, 12 pages, (2022).*
"Louvain_method," Wikipedia, downloaded Oct. 1, 2022 from: https://en.wikipedia.org/wiki/Louvain_method, 4 pages, (2022).*
"PageRank," Wikipedia, downloaded Oct. 1, 2022 from: https://en.wikipedia.org/wiki/PageRank, 16 pages, (2022).*
Wang, Pei, Xinghuo Yu, and Jinhu Lü. "Identification and evolution of structurally dominant nodes in protein-protein interaction networks." IEEE transactions on biomedical circuits and systems 8.1 (2014): 87-97.*
Abdel-Fattah, M., et al. "Modulation of brain ACE and ACE2 may be a promising protective strategy against cerebral ischemia/reperfusion injury: an experimental trial in rats," Naunyn-Schmiedeberg's Archives of Pharmacology, 2018, 391(9), pp. 1003-1020.
Chen, M. et al. "Effect of GIV on neuroinflammary response in a model of cerebral ischemia/reperfusion injury," Acta Universitatis Medicinalis Anhui, Jan. 2023; 58(1), pp. 54-59.
Chin, C.-H., et al. "cytoHubba: identifying hub objects and sub-networks from complex interactome." BMC Syst Biol. 2014; 8 (Suppl 4):S11, 11 pages.
Hendler, J. "Google's PageRank and Beyond: The Science of Search Engine Rankings," Physics Today 60(2), Feb. 2007, p. 64.
Konkuk University, Dept. of Internet and Multimedia Eng. "How does Google rank webpages?", http://scenic.princeton.edu/network20q/lectures/Q3_notes.pdf, archived at https://^web.archive.org/web/20120131083328/http://scenic.princeton.edu/network26q/lectures/Q3notes.pdf, Jan. 1, 2012, 73 pages.
Langville, A.N., et al. "Google's PageRank and Beyond: The Science of Search Engine Rankings," Princeton University Press, 2006, 235 pages.
Li, N., et al. "Gene Network Mechanism of Zhilong Huoxue Tongyu Capsule in Treating Cerebral Ischemia-Reperfusion," Frontiers in Pharmacology, Jul. 2022, 13, pp. 1-12.
McPherson, C.A., et al. "Interleukin (IL)-1 and IL-6 regulation of neural progenitor cell proliferation with hippocampal injury: differential regulatory pathways in the subgranular zone (SGZ) of the adolescent and mature mouse brain," Brain Behav Immun., Jul. 2011;25(5), pp. 850-862.
Page, L. "The Page Rank Citation Ranking: Bringing Order to the Web," Technical report, Computer Science Department, Stanford University, Jan. 29, 1998, 17 pages.
Peng, W., et al. "Identification of Protein Complexes Using Weighted PageRank-Nibble Algorithm and Core-Attachment Structure," IEEE/ACM Trans Comput Biol Bioinform., Jan./Feb. 2015, 12(1), pp. 179-192.
Shimbel, A. "Structural parameters of communication networks," The Bulletin of Mathematical Biophysics, 1953; 15, pp. 501-507.
Zhao, B., et al. "An iteration method for identifying yeast essential proteins from heterogeneous network," BMC Bioinformatics, 2019, 20, 13 pages.

* cited by examiner

*Primary Examiner* — G. Steven Vanni
(74) *Attorney, Agent, or Firm* — Lewis Roca Rothgerber Christie LLP (57) ABSTRACT

A method for identifying a key module and a key node of a biomolecular complex network by fusing multiple methods on the basis of a topological structure of the biomolecular complex network which may be such as a protein-protein interaction network, a gene expression regulation network, a biological metabolism network, an epigenetic network, a phenotypic network or a signaling network, comprising the following main steps: according to the biomolecular network and a module division for the network, comprehensively and quantitatively identifying the key module and key node on the basis of the topological structure by various measuring methods from multi-angle.

9 Claims, 9 Drawing Sheets

METHOD FOR IDENTIFYING KEY MODULE OR KEY NODE IN BIOMOLECULAR NETWORK

CROSS-REFERENCE TO RELATED APPLICATION(S)

This application is a U.S. National Phase Patent Application of International Application Number PCT/CN2017/071209, filed on Jan. 16, 2017, which claims priority of Chinese Patent Application Number 201610269466.0, filed on Apr. 27, 2016, the entire contents of all of which are incorporated herein by reference.

TECHNICAL FIELD

The present invention relates to the field of biological information technology. Specifically, the present invention relates to a method for identifying core module(s) or core node(s) in a complex molecular network that is intervened with disease and drug, such as protein-protein interaction networks, gene expression regulatory networks, drug metabolic networks and networks of drug targets and the like.

BACKGROUND OF THE INVENTION

With the advent of the era of omics and the development of high-throughput technologies, a huge amount of biological data sets have been produced, and common biomolecular networks have emerged accordingly, for example, protein-protein interaction networks, gene expression regulatory networks, drug metabolic networks and the like. Effective analysis of these data networks can reveal mechanisms of, such as gene expression regulations, protein-protein interactions, and metabolite interactions, which can then be applied in the fields of mechanism research and treatment of disease and drug development and so on.

Evidences show that there is a module structure in a biomolecular network, and its identification helps to reduce the dimensionality of a complex network and simplify the complex network. Thus, the module structure is a key factor in understanding biological systems and can provide an opportunity to systematically reveal complicated mechanisms of drug action. Moreover, a network data model shows that, in case of complex diseases, it is more effective to inhibit multiple targets than to inhibit a single target. Therefore, treatments of complex diseases require a modularity design to affect multiple targets, and also require identification of modules in related systems and networks.

However, although multiple modules exist in a biomolecular network, they are of unequal status and can be divided into domination and subordination. The inventors of the present invention has proposed in previous researches that there are core modules in a biological molecular network, and they should be modules occupying key and dominant positions in both structure and function, that is to say, the core modules have strong centrality and dominance structurally and strong integration functionally, and can trigger one or more specific effects.

As is known to all, the key to solve a problem is to catch the main contradiction in complex matters. At present, even though researchers have carried out work in identifying core modules, those existing studies always ignore the topological structure of the module network and the impact of the relationship between modules on core modules, and lack quantitative analysis of core modules or core nodes.

Therefore, there is still a need in the art to provide a novel method for identifying core module(s) or core node(s) in a complex biomolecular network.

SUMMARY OF THE INVENTION

In view of the above technical problems, the present invention is to provide a novel method for identifying core module(s) or core node(s) in a biomolecular network. The method can identify core module(s) or core node(s) from a biomolecular network based on multiple methods for measuring important nodes and topological structures of the network or module.

Definition

As used herein, the term "biomolecular network" refers to a network existing in a biological system in different organizational forms, and is composed of nodes representing various biomolecules and edges representing interaction relationships between the biomolecules. Common biomolecular networks can be gene transcription regulatory networks, biological metabolic networks, epigenetic networks, phenotype networks, signaling pathway networks, protein-protein interaction networks and the like.

As used herein, the term "core module" refers to a module occupying key and dominant positions in both structure and function in a network, that is to say, the module has a centrality structurally and a strong integration functionally, and the impact of deleting the module on the network structure and information transmission exceeds the average impact of deleting other modules in the network on the network structure and information transmission; meanwhile, the module can trigger one or more specific effects.

As used herein, the term "core node" refers to a node occupying key positions in both structure and function in a network. For example, the node has important influences on the information transmission and the interaction between nodes and the like in the network, and the impact of deleting it on the network structure and information transmission exceeds the average impact of deleting other nodes in the network on the network structure and information transmission. As the core node plays an important role in the whole biomolecular network (such as a protein-protein interaction network), it can be regarded as a driver that has a driving role in pharmacology. Therefore, the core node herein is also called a "pharmacological driver".

Technical solutions provided by the present invention are as follows.

In one aspect, the present invention provides a method for identifying core module(s) in a complex biomolecular network, the method comprises the following steps:

(1) Identifying the biomolecular network for modules by taking the number of nodes ≥3 as a standard; an exemplary method for identifying modules is MCODE.

(2) For the modules identified in step (1), constructing a weighted or unweighted module interaction network based on component correlations between the modules. Constructing the weighted module interaction network can be carried out as follows: restoring connections of edges between the modules that actually exist in the original network to construct interactions between the modules, in which the number of the edges is taken as the weight of the relationship between the modules, and the more edges connecting the nodes in two modules, the greater weight of the edges of the interaction between the two modules; while constructing the unweighted module interaction network only takes the existence of edges between modules as a standard, and the edges between all modules are regarded as one.

(3) For the weighted or unweighted module interaction network constructed in step (2), identifying core module(s) using at least three methods for measuring node importance, wherein a module is identified as a core module if the following conditions are satisfied by the module: values obtained by calculating all the modules in the network according to the methods for measuring node importance are ranked in descending order for each method respectively, and (A) at least one value of the module ranks first with the corresponding method for measuring node importance; and (B) all the values of the module rank among the top three with the corresponding methods for measuring node importance.

Preferably, the biomolecular network is selected from the group consisting of a gene expression regulatory network, a protein-protein interaction network, a biological metabolic network, an epigenetic network, a phenotype network, a signaling pathway network, and the like; more preferably, the biomolecular network is a protein-protein interaction network; further preferably, the biomolecular network is a disease-related protein-protein interaction network; further more preferably, the biomolecular network is a disease-related protein-protein interaction network before or after drug intervention. Since the biomolecular network of the present invention can be a disease-related network and can further be combined with drug intervention, the identification method of the present invention provides a scientific basis for mechanism research of disease and development of corresponding drug by revealing key parts of data networks.

As regard to complexity, the biomolecular network is a protein-protein interaction network; preferably, the network is composed of ≥100 nodes (proteins) and ≥200 edges (interaction relationships between the proteins); more preferably, the network is composed of ≥200 nodes (proteins) and ≥500 edges (interaction relationships between the proteins); in particularly, the network is composed of ≥2000 nodes (proteins) and ≥6000 edges (interaction relationships between the proteins).

Wherein, the method for measuring node importance as described in step (3) of the present invention is selected from the group consisting of methods of Degree centrality, Closeness centrality, Eigenvector centrality, Betweenness centrality, Subgraph centrality, Hub centrality, Control centrality, Weighted degree, Stress, PageRank and Spectrum of the adjacency matrix. See Table 1 below for details.

TABLE 1 various methods for measuring node importance

Degree centrality
Closeness centrality
Eigenvector centrality
Betweenness centrality
Subgraph centrality
Hub centrality
Control centrality
Weighted degree
Stress
PageRank
Spectrum of the adjacency matrix In another aspect, the present invention provides a method for identifying core node(s) in a network or module, the method comprises the following steps: identifying core node(s) in the network or module using at least three methods for measuring node importance, wherein a node is identified as a core node if the following conditions are satisfied by the node: values obtained by calculating all the nodes in the network or module according to the methods for measuring node importance are ranked in descending order for each method respectively, and (A) at least one value of the node ranks first with the corresponding method for measuring node importance; and (B) all the values of the node rank among the top three with the corresponding methods for measuring node importance.

The core node can be identified either from any network, such as a biomolecular networks, or from the module obtained from step (1) or (2) of the above method respectively.

Therefore, when identifying core node(s) from a network, the network is preferably a biomolecular network, which is selected from the group consisting of a gene expression regulatory network, a protein-protein interaction network, a biological metabolic network, an epigenetic network, a phenotype network, a signaling pathway network, and the like; more preferably, the biomolecular network is a protein-protein interaction network; further preferably, the biomolecular network is a disease-related protein-protein interaction network; further more preferably, the biomolecular network is a disease-related protein-protein interaction network before or after drug intervention.

As regard to complexity, the biomolecular network is a protein-protein interaction network; preferably, the network is composed of ≥100 nodes (proteins) and ≥200 edges (interaction relationships between the proteins); more preferably, the network is composed of ≥200 nodes (proteins) and ≥500 edges (interaction relationships between the proteins); in particularly, the network is composed of >2000 nodes (proteins) and ≥6000 edges (interaction relationships between the proteins).

When identifying core node(s) from a module, the module is preferably a module obtained from identifying a biomolecular network by taking the number of nodes ≥3 as a standard.

Or the module is a core module obtained through the following steps:

(1) Identifying the biomolecular network for modules by taking the number of nodes ≥3 as a standard.

(2) For the modules identified in step (1), constructing a weighted or unweighted module interaction network based on component correlations between the modules.

Constructing the weighted module interaction network can be carried out as follows: restoring connections of edges between the modules that actually exist in the original network to construct interactions between the modules, in which the number of the edges is taken as the weight of the relationship between the modules, and the more edges connecting the nodes in two modules, the greater weight of the edges of the interaction between the two modules; while constructing the unweighted module interaction network only takes the existence of edges between modules as a standard, and the edges between all modules are regarded as one.

(3) For the weighted or unweighted module interaction network constructed in step (2), identifying core module(s) using at least three methods for measuring node importance, wherein a module is identified as a core module if the following conditions are satisfied by the module: values obtained by calculating all the modules in the network according to the methods for measuring node importance are ranked in descending order for each method respectively, and (A) at least one value of the module ranks first with the corresponding method for measuring node importance; and (B) all the values of the module rank among the top three with the corresponding methods for measuring node importance.

Further, a method for identifying core node(s) comprises the following steps:

(1) Identifying the biomolecular network for modules by taking the number of nodes ≥3 as a standard.

(2) For the modules identified in step (1), constructing a weighted or unweighted module interaction network based on component correlations between the modules.

Constructing the weighted module interaction network can be carried out as follows: restoring connections of edges between the modules that actually exist in the original network to construct interactions between the modules, in which the number of the edges is taken as the weight of the relationship between the modules, and the more edges connecting the nodes in two modules, the greater weight of the edges of the interaction between the two modules; while constructing the unweighted module interaction network only takes the existence of edges between modules as a standard, and the edges between all modules are regarded as one.

(3) For the weighted or unweighted module interaction network constructed in step (2), identifying core module(s) using at least three methods for measuring node importance, wherein a module is identified as a core module if the following conditions are satisfied by the module: values obtained by calculating all the modules in the network according to the methods for measuring node importance are ranked in descending order for each method respectively, and (A) at least one value of the module ranks first with the corresponding method for measuring node importance; and (B) all the values of the module rank among the top three with the corresponding methods for measuring node importance.

(4) For the core module(s) identified in step (3), identifying core node(s) in the core module(s) using at least three methods for measuring node importance, wherein a node is identified as a core node if the following conditions are satisfied by the node: values obtained by calculating all the nodes in the network or module according to the methods for measuring node importance are ranked in descending order for each method respectively, and (A) at least one value of the node ranks first with the corresponding method for measuring node importance; and (B) all the values of the node rank among the top three with the corresponding methods for measuring node importance.

Wherein, the method for measuring node importance as described in steps (3) and (4) is selected from the group consisting of methods of Degree centrality, Closeness centrality, Eigenvector centrality, Betweenness centrality, Subgraph centrality, Hub centrality, Control centrality, Weighted degree, Stress, PageRank and Spectrum of the adjacency matrix. See also Table 1.

Figure 1:
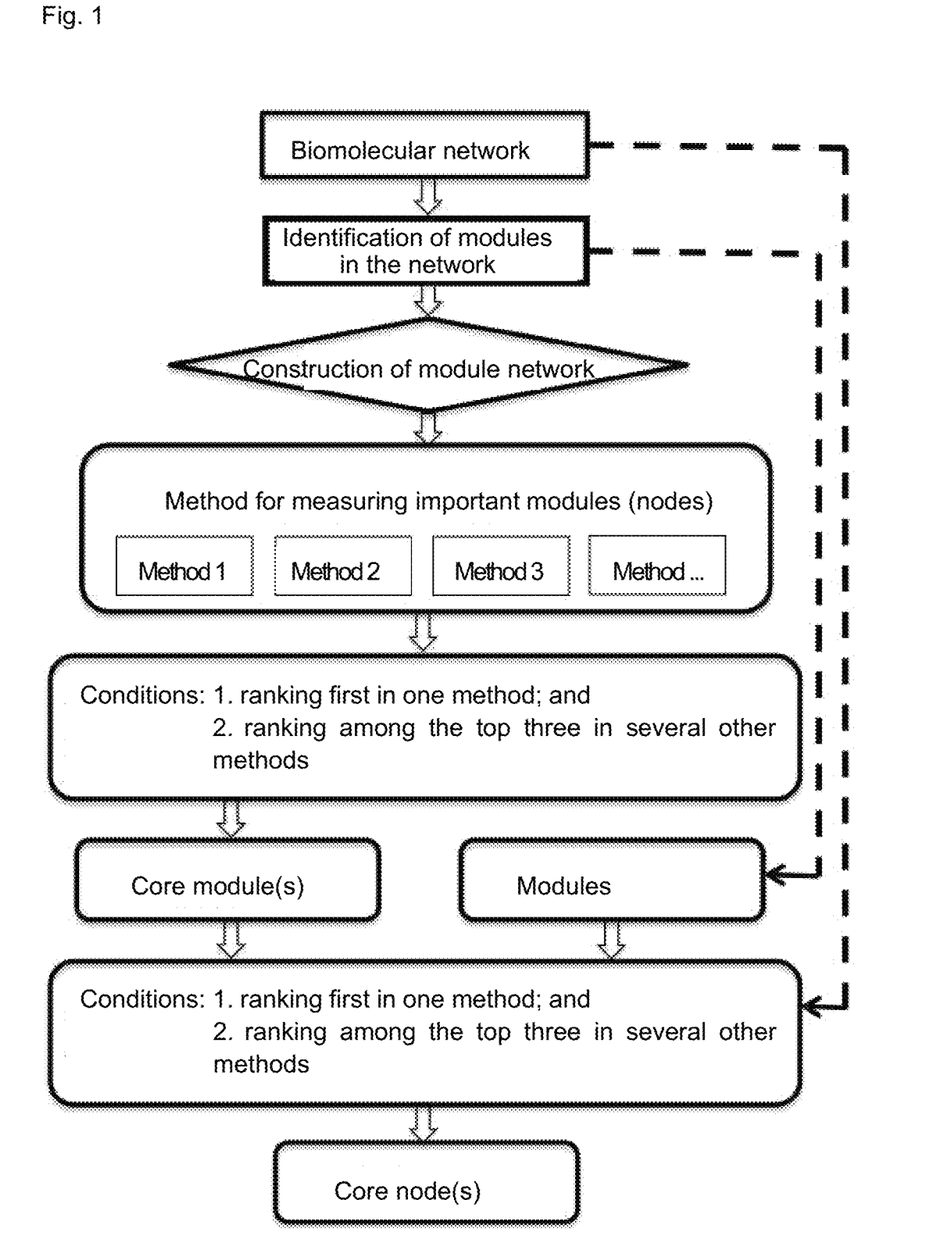
FIG. 1 shows a flowchart of the present method for identifying core module(s) and pharmacological driver(s).

The identification method provided by the present invention can be seen in FIG. 1.

According to a specific embodiment of the present invention, the biomolecular network is a protein-protein interaction network in case of cerebral ischemia.

Especially, the biomolecular network is a protein-protein interaction network derived from a cerebral ischemia model group, a baicalin group or a jasminoidin group; wherein, the protein-protein interaction network derived from the cerebral ischemia model group is composed of 3750 nodes and 9162 edges, the protein-protein interaction network derived from the baicalin group is composed of 2813 nodes and 6217 edges, and the protein-protein interaction network derived from the jasminoidin group is composed of 3416 nodes and 7581 edges (see Yingying ZHANG, Identify and Compare the Core Module from Network of Protein-protein Interation after Different Compound of Qingkailing Treatments on Cerebral Ischemia Models [Doctoral thesis], CHINA ACADEMY CHINESS MEDICAL SCIENCES, 2014).

Exemplarily, a method for identifying core module(s) or core node(s) from the above four protein-protein interaction networks respectively is as follows:

(1) Identifying modules using MCODE by taking the number of nodes ≥3 as a standard;

(2) For the modules identified in step (1), constructing a weighted or unweighted module interaction network based on component correlations between the modules;

(3) For the weighted module interaction network constructed in step (2), identifying core module(s) using three methods for example, Weighted degree, Betweenness centrality and PageRank which are selected from various methods for measuring node importance; wherein a module is identified as a core module if the following conditions are satisfied by the module: values obtained by calculating all the modules in the network according to the methods for measuring node importance are ranked in descending order for each method respectively, and (A) at least one value of the module ranks first with the corresponding method; and (B) all the values of the module rank among the top three with the corresponding methods; or for the unweighted module interaction network constructed in step (2), identifying core module(s) using three methods for example, Weighted degree, Betweenness centrality and PageRank which are selected from various methods for measuring node importance; wherein a module is identified as a core module if the following conditions are satisfied by the module: values obtained by calculating all the modules in the network according to the methods for measuring node importance are ranked in descending order for each method respectively, and (A) at least one value of the module ranks first with the corresponding method; and (B) all the values of the module rank among the top three with the corresponding methods; (4) For the core module(s) identified in step (3), identifying core node(s) (pharmacological driver(s)) in the module(s) using three methods for example, Degree centrality, Betweenness centrality and PageRank, or Stress, Weighted degree and Eigenvector centrality which are selected from various methods for measuring node importance; wherein a node is identified as a core node if the following conditions are satisfied by the node: values obtained by calculating all the nodes in the module according to the methods for measuring node importance are ranked in descending order for each method respectively, and (A) at least one value of the node ranks first with the corresponding method; and (B) all the values of the node rank among the top three with the corresponding methods.

Modules, either in a complex network or as sub-networks, are all consisted of nodes and relationships (edges) between the nodes. Modules are of different status in a network, and so are nodes in a module. In fact, the core nodes have different functions on the networks or the modules. Hub nodes can be divided into party nodes and date nodes, and removing these two kinds of nodes may result in completely different impact on the topological structure of the network. Meanwhile, the identification of core modules or core nodes is very important to understand the functionary mechanism of the entire network. For example, when an infectious disease is spreading, the identification of important nodes can help to understand the dynamic process of the spreading of the infectious disease better, and then serious consequences may be prevented possibly by using effective methods. Therefore, it is of great significance to study the importance of modules or nodes in complex biomolecular networks, especially those related to diseases and drugs, for controlling or reversing the development of diseases and designing drugs.

In this regard, an innovational concept of identifying core modules and core nodes (i.e. pharmacological drivers) is proposed by the present invention for complex network or module structures intervened with disease and drug. Meanwhile, a method for identifying core module(s) and core node(s) from a biomolecular network is provided in view of the concept. In a specific identification process, various methods for measuring important nodes and topological characteristics of the network modules are combined to quantitatively identify core module(s) and pharmacological driver(s). Specifically, as structure determines function, the method of the present invention gives sufficient attention to the topological structure of the network no matter in constructing molecular network and module network, partitioning modules, or identifying core modules and drivers. What's more, core modules are determined by the method of the present invention through multi-angle quantitative analysis of the module itself, the module network as a whole, and the relationship between the modules, and pharmacological drivers are determined through multi-method comprehensive quantitative analysis of local, global and iterative importance. The research on core modules and pharmacological drivers lays a foundation for exploring main pharmacological mechanism that produces synergistic effects in drug combination, lays roots for analyzing drug-drug interactions, guiding the combination of drugs and treating diseases, and provides scientific basis for disease treatment and drug development.

BRIEF DESCRIPTION OF THE DRAWINGS

Hereinafter, embodiments of the present invention will be described in detail with reference to the accompanying drawings, in which:

FIG. 7 shows verification results of pharmacological drivers in the core module $M_{JA-1}$ of jasminoidin group. The figure shows effects on the characteristic path length of the module by removing individual nodes in the module, in which the abscissa represents the name of removed individual nodes ("none" means no node is removed), and the ordinate corresponds to the value of the characteristic path length of the module when removing individual nodes. It can be seen that the removal of 116 has the greatest impact on the module, which is consistent with the result identified by the method of the present invention.

DETAILED DESCRIPTION OF PREFERRED EMBODIMENTS

The present invention will be further described in detail in combination with the particular embodiments hereinafter. It will be appreciated by those skilled in the art that the embodiments provided are only used to illustrate the present invention, rather than limiting the scope of the present invention in any way.

Experimental methods in the following embodiments, if no any other specific instruction is provided, are all conventional methods. Medicinal materials, reagent materials and the like used in the following examples, if no source of purchase is provided, are conventional products that can be commercially available.

The object of the present invention is to identify core modules and pharmacological drivers from the biomolecular networks intervened with diseases and drug, which may then provide a basis for guiding disease treatment and drug development. The effectiveness and feasibility of the present method is proved by following examples.

These examples are non-limiting and the present method can also be applied to other types of networks.

Example 1 Identification and Verification of Core Modules

Figure 2A:
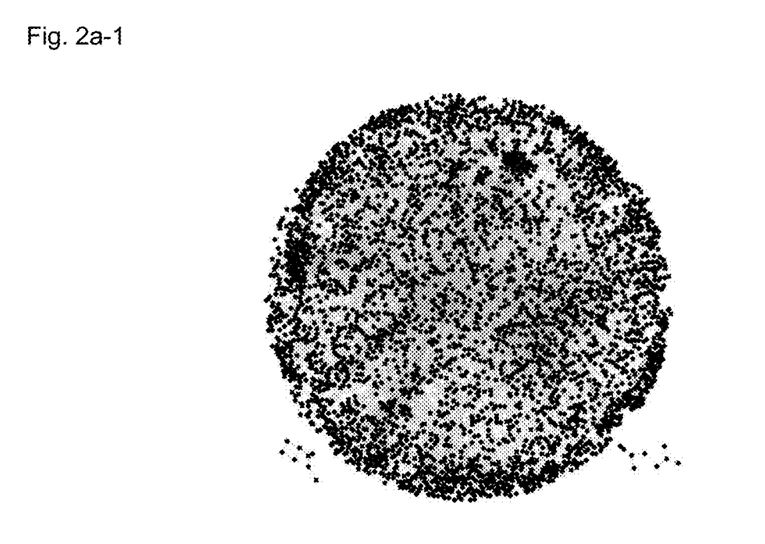
FIG. 2 shows the protein-protein interaction networks of cerebral ischemia model group and of each group intervened with effective components of Qingkailing respectively. The circular structures showed in panels 2a-1, 2b-1 and 2c-1 are the protein-protein interaction networks of cerebral ischemia model group, baicalin (a component of Qingkailing) group and jasminoidin (a component of Qingkailing) group respectively. Panels 2a-2, 2b-2 and 2c-2 show results of the degree distribution of the nodes in the corresponding networks, and the abscissas represent the degrees of the nodes, and the ordinates represent the number of nodes. It can be seen from the figure that each network belongs to a scale-free network.
Figure 2A:
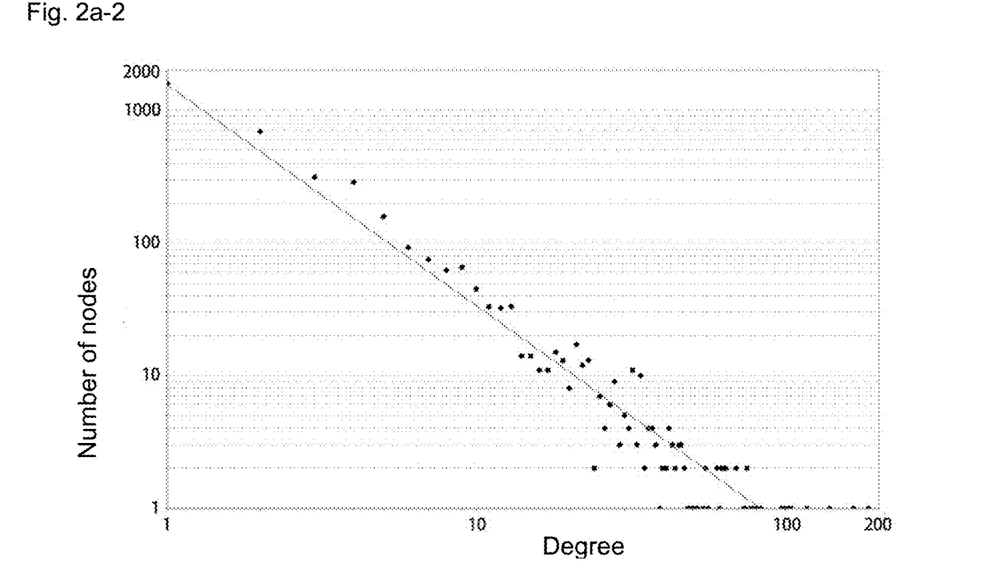

The protein-protein interaction networks of mouse models of cerebral ischemia intervened with components of Qingkailing were used (FIG. 2; see Yingying ZHANG, Identify and Compare the Core Module from Network of Protein-protein Interation after Different Compound of Qingkailing Treatments on Cerebral Ischemia Models [Doctoral thesis], CHINA ACADEMY CHINESS MEDICAL SCIENCES, 2014):

Protein-protein interaction network of cerebral ischemia model group (Vehicle group) (panel 2a-1), which was composed of 3750 nodes and 9162 edges.

Figure 2B:
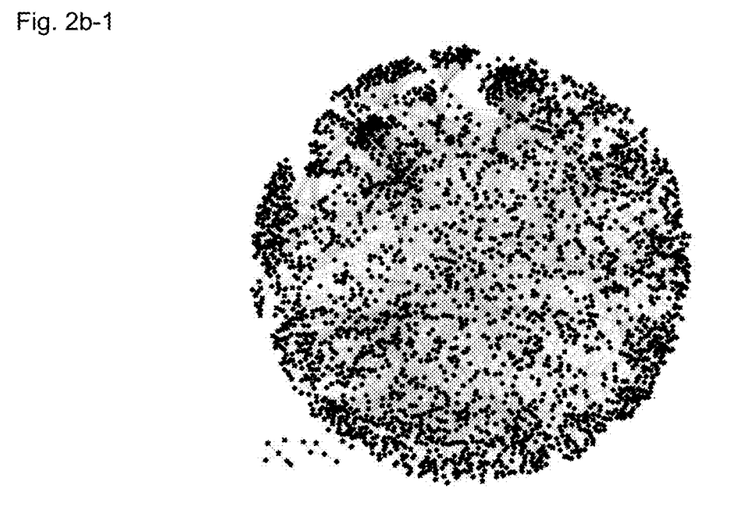
Figure 2B:
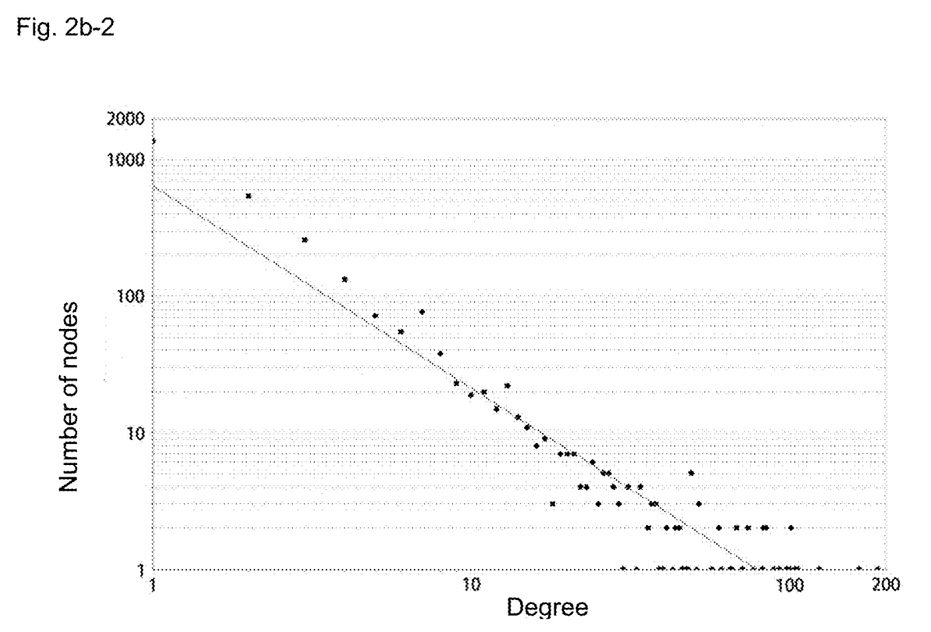

Protein-protein interaction network of baicalin group (BA group) (panel 2b-1), which was a protein-protein interaction network obtained by intervening the cerebral ischemia model with the drug baicalin and was composed of 2813 nodes and 6217 edges.

Figure 2C:
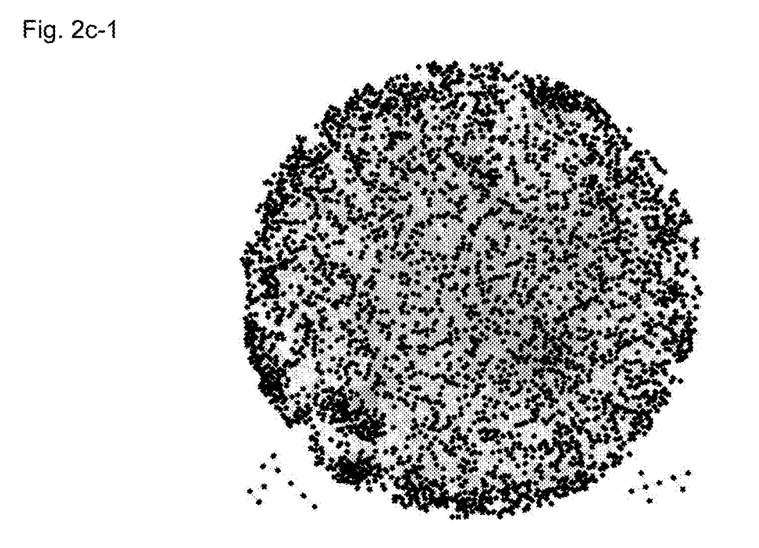
Figure 2C:
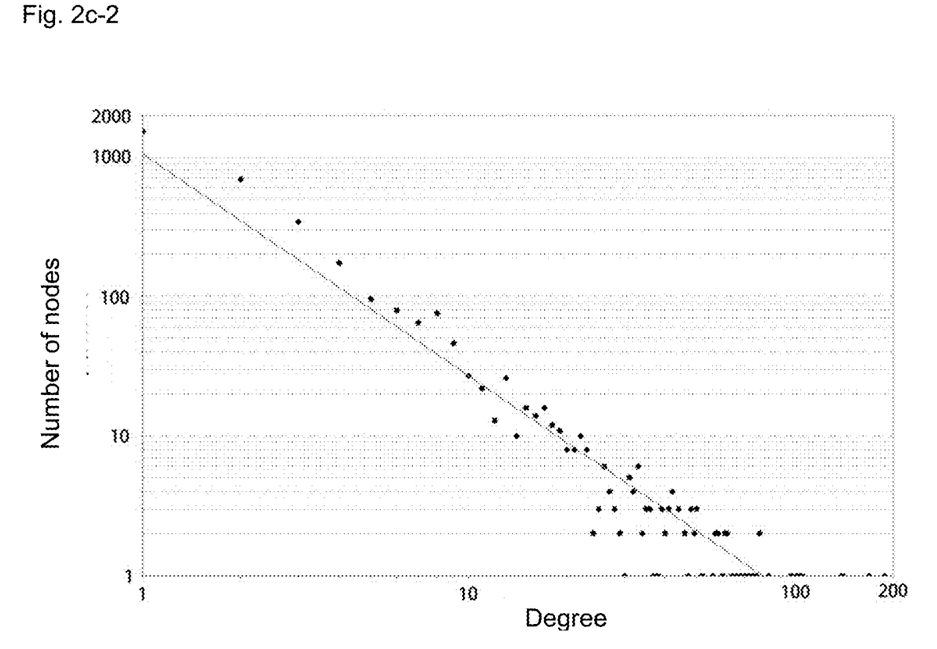

Protein-protein interaction network of jasminoidin group (JA group) (panel 2c-1), which was a protein-protein interaction network obtained by intervening the cerebral ischemia model with the drug jasminoidin and was composed of 3416 nodes and 7581 edges.

Figure 3A:
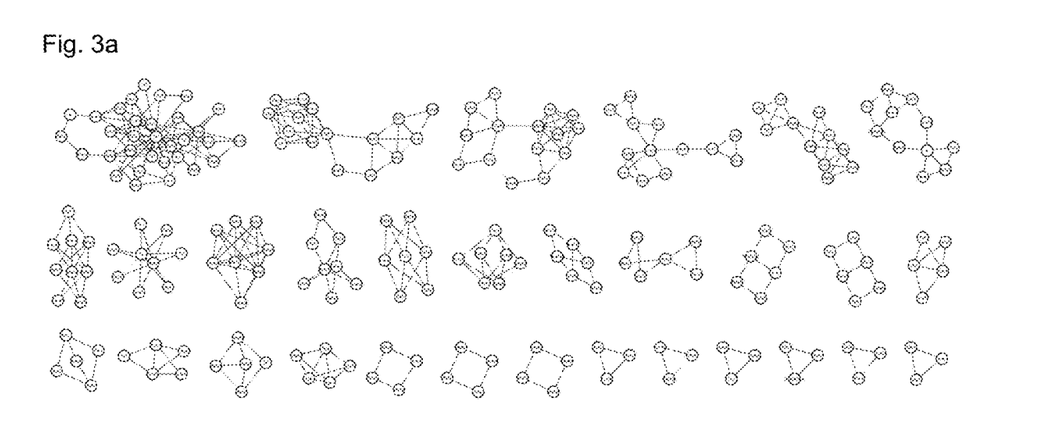
FIG. 3 shows results of identifying modules from the protein-protein interaction networks of cerebral ischemia model group and of each group intervened with effective components of Qingkailing respectively.
Figure 3B:
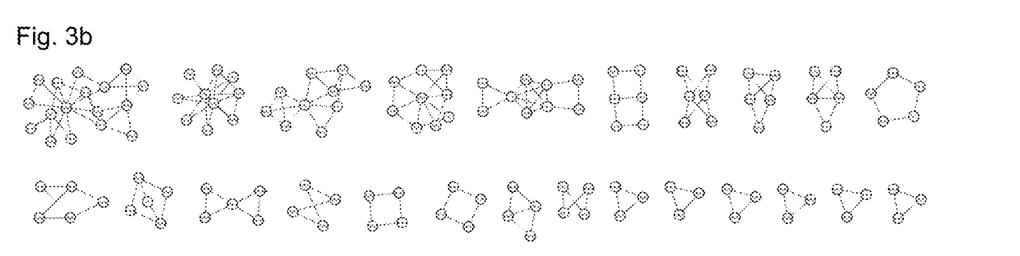
Figure 3C:
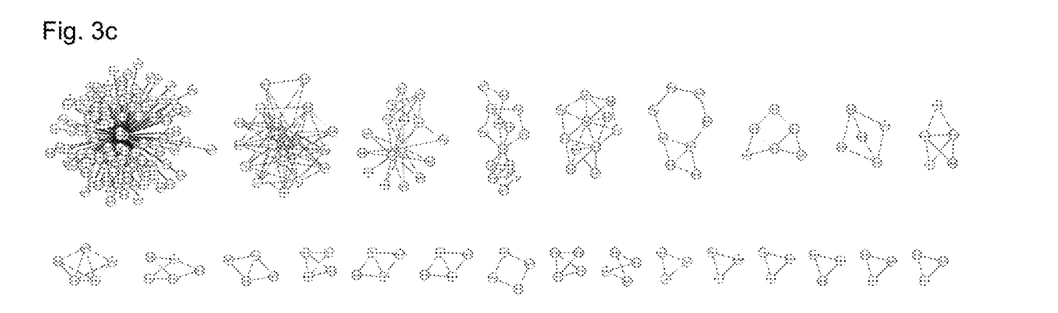

Process of identifying core modules and pharmacological drivers was as follows: Step 1: Module identifications were conducted on each network using MCODE. The results are shown in FIG. 3, in which modules identified from the protein-protein interaction network of the cerebral ischemia model group are shown in panel 3a, and modules identified from the protein-protein interaction network of the baicalin group are shown in panel 3b, and modules identified from the protein-protein interaction network of the jasminoidin group are shown in panel 3c.

Figure 4A:
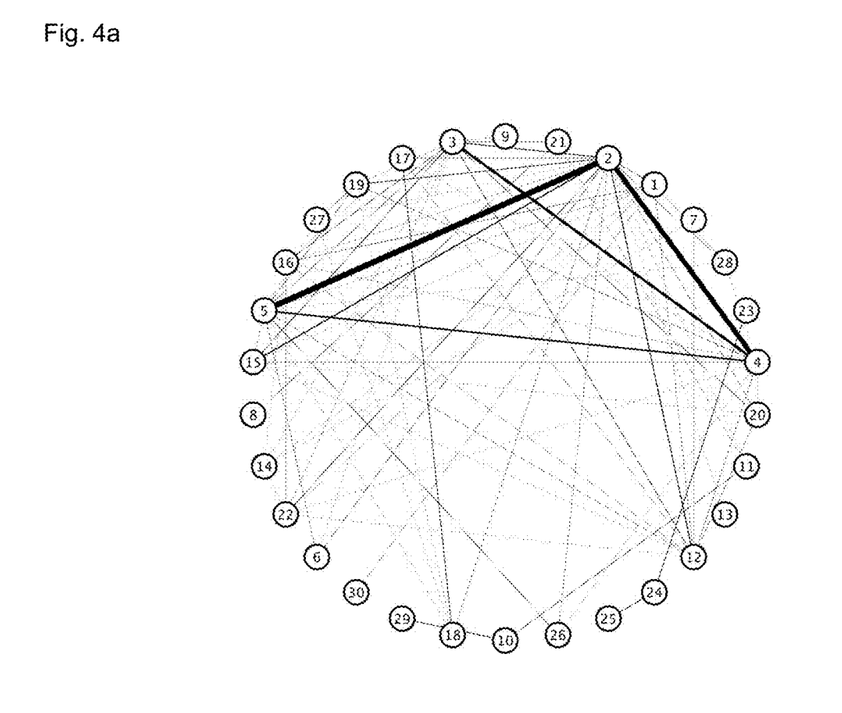
FIG. 4 shows weighted module interaction networks, which are constructed based on the protein-protein interaction networks of cerebral ischemia model group and of each group intervened with effective components of Qingkailing respectively. The circles in the figure represent modules and the edges represent the interactions between the modules. The thickness of the edges indicate the number of connecting edges between the modules, and the thicker the edges, the greater the number of the connecting edges.
Figure 4B:
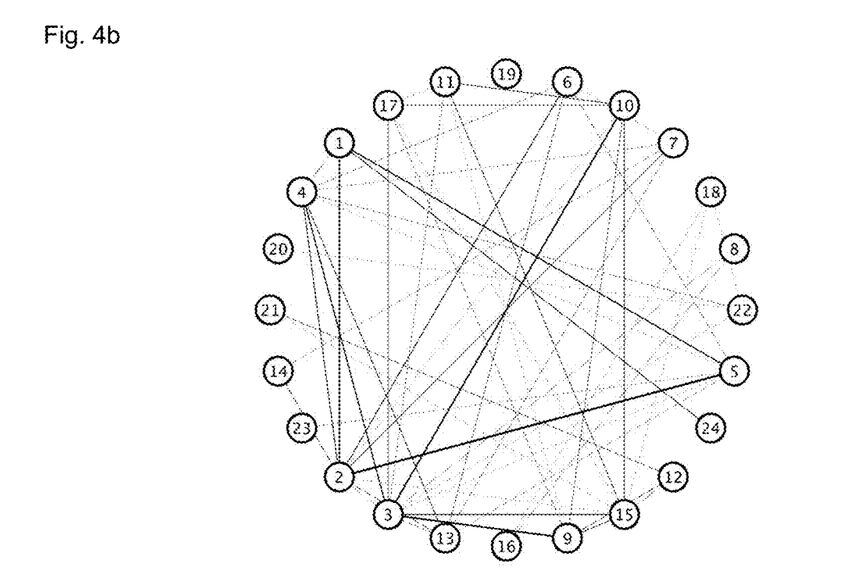
Figure 4C:
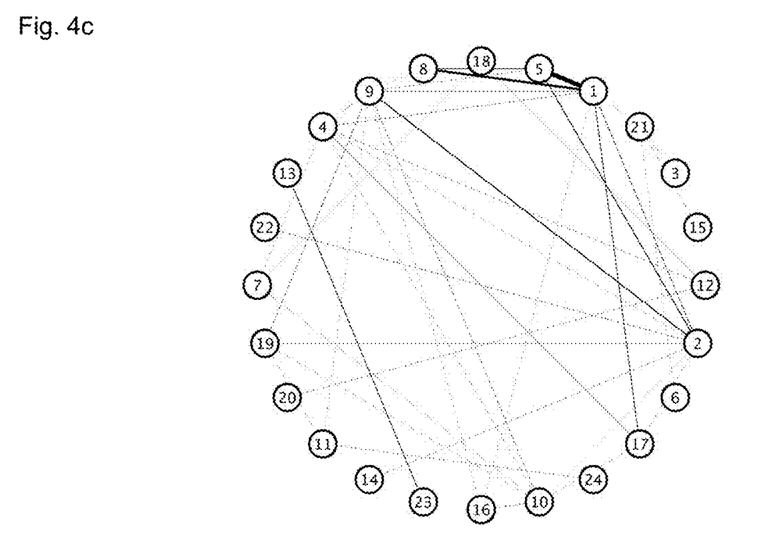

Step 2: Weighted module interaction networks were constructed based on component correlations between the modules. The results are shown in FIG. 4, in which the weighted module interaction network of the cerebral ischemia model group is shown in panel 4a, the weighted module interaction network of the baicalin group is shown in panel 4b, and the weighted module interaction network of the jasminoidin group is shown in panel 4c.

Step 3: Core modules were identified using three methods including Weighted degree, Betweenness centrality and PageRank that were selected from various methods for measuring node importance; wherein a module was identified as a core module only if the following conditions were satisfied by the module: values obtained by calculating all the modules in the network according to the methods for measuring node importance were ranked in descending order for each method respectively, and (A) at least one value of the module ranked first with one corresponding method; and (B) all the values of the module ranked among the top three with all the other corresponding methods.

The results showed that, in each group, the module ranked first with each method was among the top three with other methods, and the specific results are shown in Table 2-4 below. In each Table, the first column represents the ranking of the calculated values according to each method; the number in front of parentheses in each row represents the module's number, and the values in parentheses are the values of modules calculated according to the method. Except for values calculated according to the method of Weighted degree, values calculated according to the other two methods were rounded to the third decimal place. The calculated values according to each method were ranked in descending order, and the core module identified was marked in the last column.

TABLE 2

Identification results of core modules in the weighted module network of the Vehicle group

| Vehicle group | Weighted degree | Betweenness centrality | PageRank | |
|---|---|---|---|---|
| 1 | 2 (25.100) | 2 (254.946) | 2 (0.107) | Core module ($M_{Vehicle-2}$) |
| 2 | 4 (15.900) | 3 (148.407) | 3 (0.800) | |
| 3 | 5 (14.300) | 11 (105.8) | 5 (0.069) | |
| 4 | 3 (9.500) | 1 (62.849) | 4 (0.067) | |

TABLE 2-continued

Identification results of core modules in the weighted module network of the Vehicle group

| Vehicle group | Weighted degree | Betweenness centrality | PageRank |
|---|---|---|---|
| 5 | 12 (4.200) | 21 (57.2) | 12 (0.063) |
| 6 | 15 (3.800) | 12 (51.214) | 1 (0.055) |
| 7 | 19 (2.500) | 10 (50) | 16 (0.046) |
| 8 | 1 (2.200) | 5 (48.03) | 22 (0.041) |
| 9 | 16 (2.100) | 4 (29.267) | 15 (0.041) |
| 10 | 10 (1.600) | 16 (12.844) | 19 (0.036) |

TABLE 3

Identification results of core modules in the weighted module network of the baicalin group

| baicalin group | Weighted degree | Betweenness centrality | PageRank | |
|---|---|---|---|---|
| 1 | 3 (8.600) | 3 (161) | 3 (0.091) | Core module ($M_{BA-3}$) |
| 2 | 2 (8.300) | 15 (108.667) | 2 (0.081) | |
| 3 | 5 (5.000) | 2 (100.567) | 15 (0.077) | |
| 4 | 15 (4.500) | 22 (55.267) | 4 (0.067) | |
| 5 | 4 (4.500) | 5 (49.333) | 5 (0.062) | |
| 6 | 10 (4.400) | 18 (43.867) | 9 (0.051) | |
| 7 | 9 (4.300) | 4 (42.1) | 13 (0.050) | |
| 8 | 1 (3.800) | 8 (37.467) | 10 (0.049) | |
| 9 | 13 (2.600) | 9 (9) | 22 (0.044) | |
| 10 | 6 (2.200) | 10 (7.4) | 16 (0.044) | |

TABLE 4

Identification results of core modules in the weighted module network of the jasminoidin group

| Jasminoidin group | Weighted degree | Betweenness centrality | PageRank | |
|---|---|---|---|---|
| 1 | 1 (11.5) | 1 (156.533) | 2 (0.099) | Core module ($M_{JA-1}$, $M_{JA-2}$) |
| 2 | 5 (8.1) | 21 (114) | 9 (0.094) | |
| 3 | 2 (4.500) | 2 (96.383) | 1 (0.088) | |
| 4 | 8 (3.900) | 9 (93.417) | 4 (0.076) | |
| 5 | 9 (3.3) | 12 (51.883) | 10 (0.074) | |
| 6 | 17 (1.3) | 11 (40) | 21 (0.073) | |
| 7 | 10 (1.2) | 10 (34.2) | 12 (0.046) | |
| 8 | 4 (1.2) | 7 (24.117) | 19 (0.046) | |
| 9 | 19 (0.9) | 19 (11.667) | 5 (0.044) | |
| 10 | 16 (0.5) | 16 (2) | 17 (0.044) | |

Figure 5A:
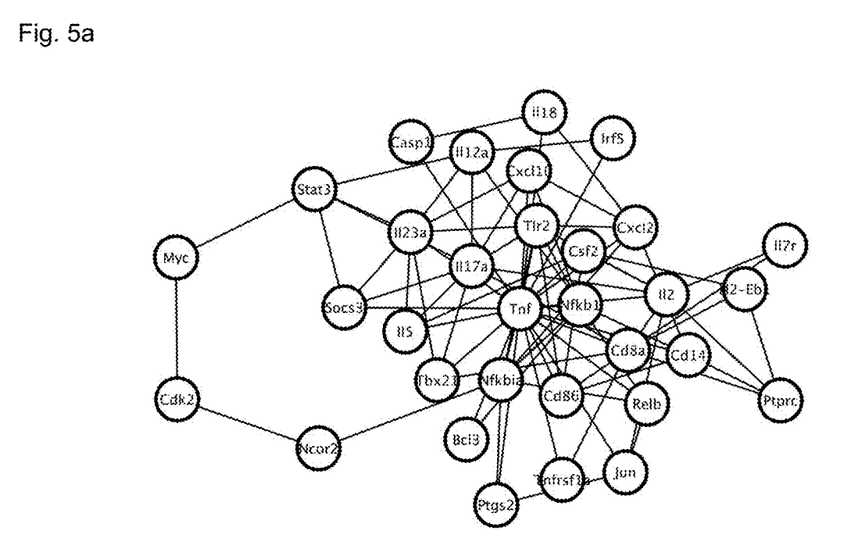
FIG. 5 shows core modules which are identified from the protein-protein interaction networks of cerebral ischemia model group and of each group intervened with effective components of Qingkailing respectively. Panels 5a, 5b and 5c show core modules of cerebral ischemia model group, baicalin (a component of Qingkailing) group and jasminoidin (a component of Qingkailing) group respectively.
Figure 5B:
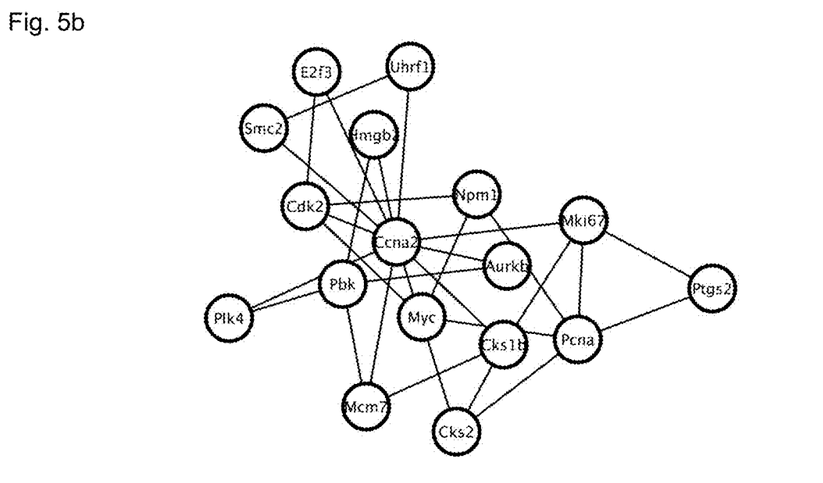
Figure 5C:
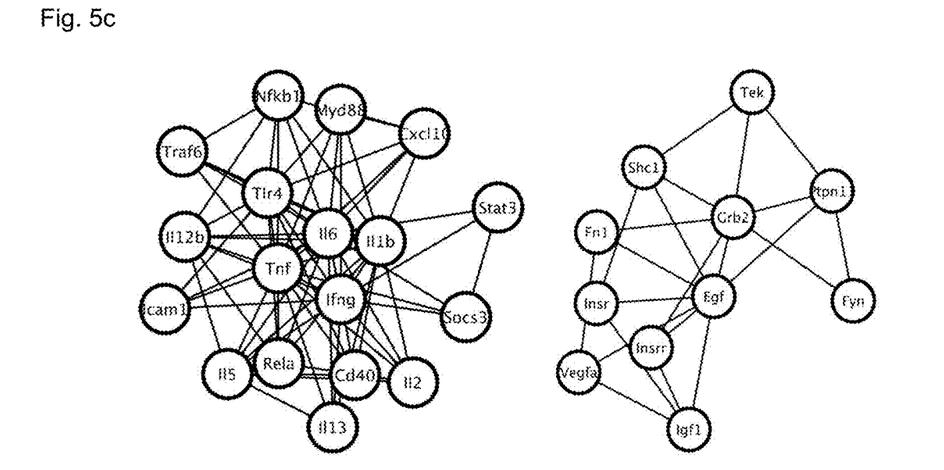

The core modules identified from each group are shown in panels 5a, 5b and 5c of FIG. 5.

In order to verify the importance of the core modules identified from the groups of cerebral ischemia model and Qingkailing components baicalin and Jasminoidin to the network, individual modules were removed from each network, and characteristic path lengths of the networks before and after the removal were observed. The results are shown in FIG. 6.

Figure 6:
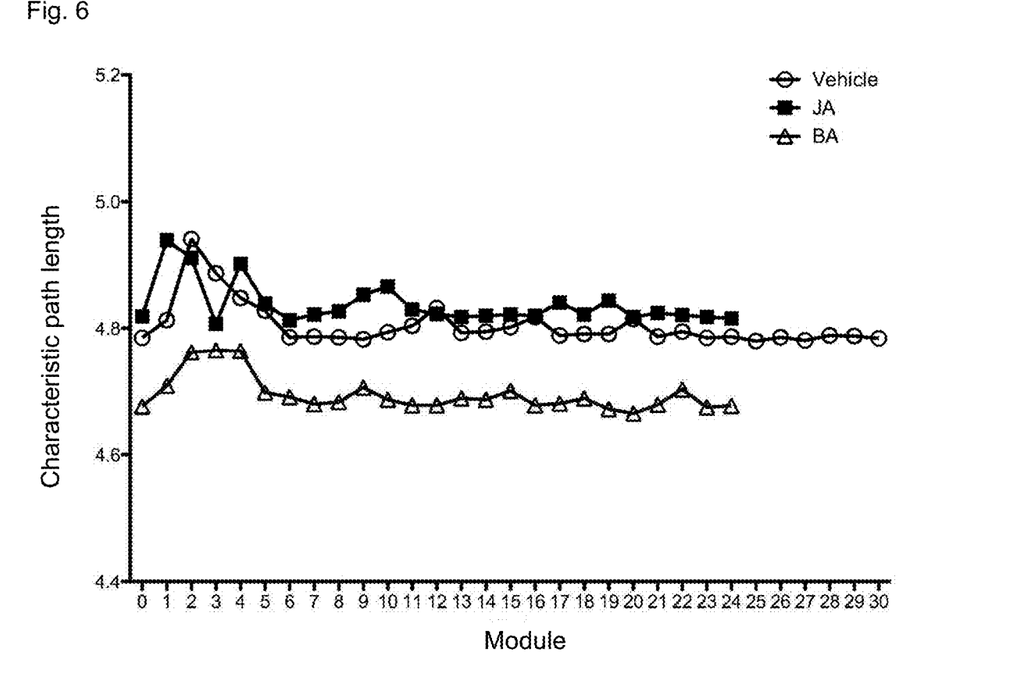
FIG. 6 shows changes in characteristic path lengths before and after removing individual modules from the protein-protein interaction networks of cerebral ischemia model group and of each group intervened with effective components of Qingkailing respectively. The abscissa represents the module's number, the ordinate represents value of the characteristic path length of the network after removing individual modules, and "0" represents value of the characteristic path length of the network without removing any module.

FIG. 6 shows the changes in the characteristic path lengths of the networks before and after respectively removing individual modules from the networks, from which it can be seen that the removal of core modules has the greatest impact on the characteristic path lengths of the networks. Meanwhile, the change in the characteristic path length of the each network after removing the core module is greater than the average change in the characteristic path length of the network after removing individual modules other than the core module, which is consistent with the identification result of each group above.

Example 2 Identification and Verification of Core Modules

In step 2, unweighted module interaction networks were constructed for the three protein-protein interaction networks (Vehicle group, BA group and JA group) described in Example 1, and then core modules and pharmacological drivers were identified.

The process was as follows:

Step 1: Module identifications were conducted on each network using MCODE.

Step 2: Unweighted module interaction networks were constructed based on component correlations between the modules.

Step 3: Core modules were identified using three methods including Degree centrality, Betweenness centrality and PageRank that were selected from various methods for measuring node importance; wherein a module was identified as a core module only if the following conditions were satisfied by the module: values obtained by calculating all the modules in the network according to the methods for measuring node importance were ranked in descending order for each method respectively, and (A) at least one value of the module ranked first with one corresponding method; and (B) all the values of the module ranked among the top three with all the other corresponding methods.

The results showed that, in each group, the module ranked first with each method was among the top three with other methods, and the specific results are shown in Table 5-7 below. In each Table, the first column represents the ranking of the calculated values according to each method; the number in front of parentheses in each row represents the module's number, and the values in parentheses are the values of modules calculated according to the method. Except for values calculated according to the method of Weighted degree, values calculated according to the other two methods were rounded to the third decimal place. The calculated values according to each method were ranked in descending order, and the core module identified was marked in the last column.

TABLE 5

Identification results of core modules in the unweighted module network of the Vehicle group

| Vehicle group | Degree centrality | Betweenness centrality | PageRank | |
|---|---|---|---|---|
| 1 | 2 (18) | 2 (254.946) | 2 (0.107) | Core module ($M_{Vehicle-2}$) |
| 2 | 3 (13) | 3 (148.407) | 3 (0.800) | |
| 3 | 4 (12) | 11 (105.8) | 5 (0.069) | |
| 4 | 5 (12) | 1 (62.849) | 4 (0.067) | |
| 5 | 12 (11) | 21 (57.2) | 12 (0.063) | |
| 6 | 1 (9) | 12 (51.214) | 1 (0.055) | |
| 7 | 16 (8) | 10 (50) | 16 (0.046) | |
| 8 | 15 (7) | 5 (48.03) | 22 (0.041) | |
| 9 | 22 (7) | 4 (29.267) | 15 (0.041) | |
| 10 | 19 (6) | 16 (12.844) | 19 (0.036) | |

TABLE 6

Identification results of core modules in the unweighted module network of the baicalin group

| baicalin group | Degree centrality | Betweenness centrality | PageRank | |
|---|---|---|---|---|
| 1 | 3 (11) | 3 (161) | 3 (0.091) | Core module ($M_{BA-3}$) |
| 2 | 2 (10) | 15 (108.667) | 2 (0.081) | |
| 3 | 15 (9) | 2 (100.567) | 15 (0.077) | |
| 4 | 4 (8) | 22 (55.267) | 4 (0.067) | |
| 5 | 5 (7) | 5 (49.333) | 5 (0.062) | |
| 6 | 10 (6) | 18 (43.867) | 9 (0.051) | |
| 7 | 9 (6) | 4 (42.1) | 13 (0.050) | |
| 8 | 13 (6) | 8 (37.467) | 10 (0.049) | |
| 9 | 6 (5) | 9 (9) | 22 (0.044) | |
| 10 | 11 (5) | 10 (7.4) | 16 (0.044) | |

TABLE 7

Identification results of core modules in the unweighted module network of the jasminoidin group

| jasminoidin group | Degree centrality | Betweenness centrality | PageRank | |
|---|---|---|---|---|
| 1 | 2 (9) | 1 (156.533) | 2 (0.099) | Core module ($M_{JA-1}$, $M_{JA-2}$) |
| 2 | 9 (9) | 21 (114) | 9 (0.094) | |
| 3 | 1 (8) | 2 (96.383) | 1 (0.088) | |
| 4 | 10 (7) | 9 (93.417) | 4 (0.076) | |
| 5 | 4 (7) | 12 (51.883) | 10 (0.074) | |
| 6 | 5 (4) | 11 (40) | 21 (0.073) | |
| 7 | 17 (4) | 10 (34.2) | 12 (0.046) | |
| 8 | 19 (4) | 7 (24.117) | 19 (0.046) | |
| 9 | 21 (4) | 19 (11.667) | 5 (0.044) | |
| 10 | 8 (3) | 16 (2) | 17 (0.044) | |

It can be seen from the results that the identification results of core modules in each group are all the same as those identified in Example 1.

Example 3 Identification and Verification of Core Nodes (i.e. Pharmacological Drivers)

Three methods of Degree centrality, Betweenness centrality and PageRank were selected to identify core nodes (i.e. pharmacological drivers) in the core module $M_{JA-1}$, which was identified from the protein-protein interaction network of jasminoidin group in Example 1; wherein a node was identified as a core node only if the following conditions were satisfied by the node: values obtained by calculating all the nodes in the network according to the methods for measuring node importance were ranked in descending order for each method respectively, and (A) at least one value of the node ranked first with one corresponding method; and (B) all the values of the node ranked among the top three with all the other corresponding methods.

It can be seen through identifying the core module $M_{JA-1}$ in the protein-protein interaction network of jasminoidin group that primary results obtained by the three methods remained consistent, that were 116. See Table 8.

TABLE 8

Identification results of core nodes in the core module $M_{JA-1}$ of the jasminoidin group

| Core module $M_{JA-1}$ | Degree centrality | Betweenness centrality | PageRank | |
|---|---|---|---|---|
| Cd40 | 6 | 0.333333333 | 0.041887251 | |
| Cxcl10 | 6 | 0.4 | 0.04226601 | |
| Icam1 | 4 | 0 | 0.030637645 | |
| Ifng | 13 | 25.46666667 | 0.086959482 | |
| Il12b | 8 | 2.366666667 | 0.053724952 | |
| Il13 | 5 | 0 | 0.036316794 | |
| Il1b | 14 | 20.33333333 | 0.090215992 | |
| Il2 | 6 | 0.733333333 | 0.042288052 | |
| Il5 | 8 | 2.266666667 | 0.054371212 | |
| Il6 | 17 | 54.66666667 | 0.111094915 | Core node (Il6) |
| Myd88 | 6 | 0.4 | 0.042102507 | |
| Nfkb1 | 7 | 1.2 | 0.048308842 | |
| Rela | 6 | 0.733333333 | 0.042138433 | |
| Socs3 | 4 | 0.666666667 | 0.032576221 | |
| Stat3 | 3 | 0 | 0.026493743 | |
| Tlr4 | 12 | 13.43333333 | 0.078686421 | |
| Tnf | 16 | 37 | 0.10363508 | |
| Traf6 | 5 | 0 | 0.036296456 | |

Core nodes were identified using a combination of other three methods. The primary results obtained by the three methods were consistent, that were Il6 too. See Table 9. Therefore, the same result can be obtained by employing any three methods.

TABLE 9

Identification results of core nodes in the core module $M_{JA-1}$ of the jasminoidin group

| Core module $M_{JA-1}$ | Stress | Weighted degree | Eigenvector centrality | |
|---|---|---|---|---|
| Cd40 | 2 | 5.631999969 | 0.198405942 | |
| Cxcl10 | 2 | 5.116999984 | 0.184767974 | |
| Icam1 | 0 | 3.862999916 | 0.139499317 | |
| Ifng | 80 | 12.52499998 | 0.304215133 | |
| Il12b | 12 | 7.170000076 | 0.239069766 | |
| Il13 | 0 | 4.435000002 | 0.167218941 | |
| Il1b | 84 | 11.97100013 | 0.342051663 | |
| Il2 | 4 | 5.716000021 | 0.186675535 | |
| Il5 | 12 | 7.487999976 | 0.225873648 | |
| Il6 | 160 | 16.00900006 | 0.373892393 | core node (Il6) |
| Myd88 | 2 | 5.654000103 | 0.194142359 | |
| Nfkb1 | 6 | 5.66900003 | 0.204461261 | |
| Rela | 4 | 4.832000077 | 0.187583177 | |
| Socs3 | 2 | 3.912999988 | 0.116864911 | |
| Stat3 | 0 | 2.872000039 | 0.082456518 | |
| Tlr4 | 56 | 11.04600006 | 0.300677336 | |
| Tnf | 132 | 15.27500015 | 0.36614353 | |
| Traf6 | 0 | 4.569000065 | 0.164631046 | |

In order to verify the importance of the core node identified to the module network, individual nodes were removed respectively from the module, and changes in characteristic path length of the module before and after the removal were observed. The results are shown in FIG. 7.

Figure 7:
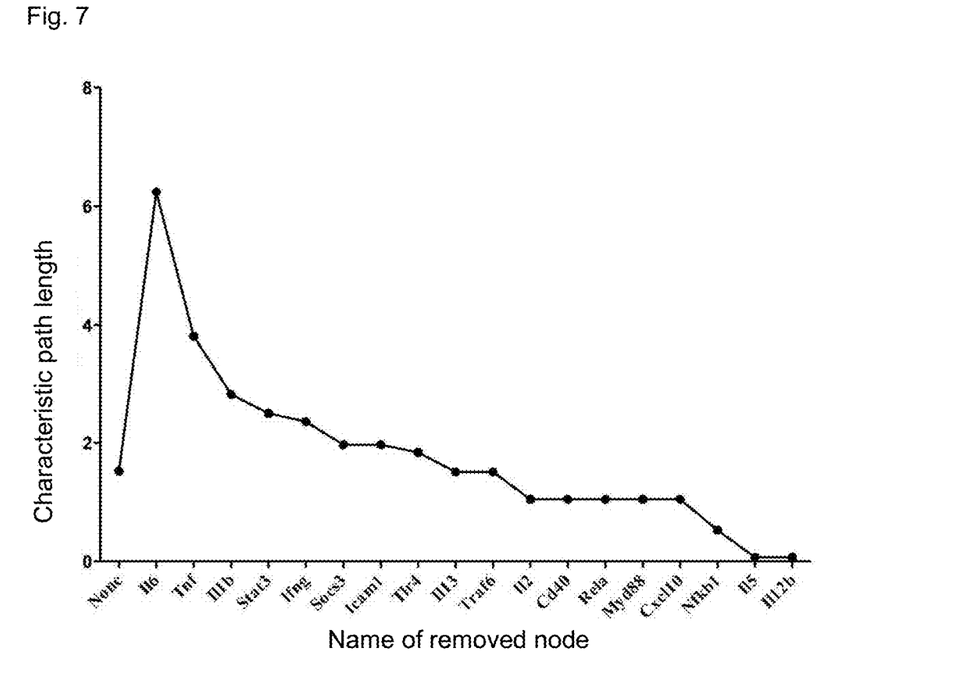

FIG. 7 shows the changes in the characteristic path length of the module before and after removing individual nodes from the modules respectively, from which it can be seen that the removal of core node Il6 has the greatest impact on the characteristic path length of the module. Meanwhile, the change in the characteristic path length of the module after removing the core node is greater than the average change in the characteristic path length of the module after removing other individual nodes, which is consistent with the identification result for the module above.

It is known through consulting literatures that Il6 is a biomarker of cerebral ischemia that is located upstream in signaling pathways in the Graft-versus-host disease and Hematopoietic cell lineage, and is of great significance for disease and treatment thereof.

It can be seen from the above Examples that the present invention conducts core module identification on protein-protein interaction networks using three methods for measuring node importance, and the module identified from each of the disease model group and the groups intervened with drugs, which ranks first with the corresponding method, is among the top three with the other corresponding methods. What's more, pharmacological drivers are identified using six methods for measuring important nodes, and the results of core nodes evaluated using multiple methods from multiple perspectives are consistent. All the results indicate that the idea and method for identifying core modules and pharmacological drivers are effective and feasible.

Although it is only exemplified in the present invention that the protein-protein interaction networks of the cerebral ischemia model group and of groups intervened with drugs are identified using specific methods for measuring node importance, core module(s) in a complex network and pharmacological driver(s) in module of a network intervened with drug(s) can also be dug out effectively using other methods for measuring important nodes in case of other network types. In particular, the identification of pharmacological drivers may not be limited to core modules; in contrast, pharmacological drivers can be divided into primary drivers and secondary drivers, which may exist in core modules and/or non-core modules, and both of which can reveal the interaction relationships between the modules and nodes in the network and provide scientific basis for disease treatment and drug development.

The above description for the embodiments of the present invention is not intended to limit the present invention, and those skilled in the art can make various changes and variations according to the present invention, which are within the protection scope of the appended claims without departing from the spirit of the invention.

What is claimed is:

1. A method of determining a pharmacological driver in a biomolecular network, the method comprising the following steps:
   (1) identifying a plurality of modules of the biomolecular network, each module of the plurality of modules having at least three nodes representing biomolecules and a plurality of edges representing interaction relationships between the biomolecules, wherein the biomolecular network is a disease-related protein-protein interaction network, and wherein the biomolecular network comprises biomolecules which are disease-related proteins;
   (2) for each module of the plurality of modules identified in step (1), constructing a weighted or unweighted module interaction network based on component correlations between the plurality of modules;
   (3) from the weighted or unweighted module interaction network constructed in step (2), identifying at least one core module using at least three first methods for measuring node importance, wherein values calculated for each of the plurality of modules according to each of the at least three first methods for measuring node importance are ranked in descending order for each respective method of the at least three first methods, and wherein a module of the plurality of modules is identified as a core module of the at least one core module in response to the following conditions being satisfied by the module: (A) at least one value of the module ranks first according to one first method of the at least three first methods for measuring node importance and (B) all the values of the module rank among a top three for each of at least two remaining first methods of the at least three first methods for measuring node importance;

(4) for the at least one core module identified in step (3), identifying the at least one core node in the at least one core module using at least three second methods for measuring node importance, wherein values calculated for each node of the at least one core module according to each of the at least three second methods for measuring node importance are ranked in descending order for each respective second method of the at least three second methods, and wherein a node of the at least one core module is identified as a core node of the at least one core node in response to the following conditions being satisfied by the node: (A) at least one value of the node ranks first according to one second method of the at least three second methods for measuring node importance and (B) all the values of the node rank among a top three for each of at least two remaining second methods of the at least three second methods for measuring node importance; and (5) utilizing the at least one core module identified in step (3) and the at least one core node identified in step (4) as the pharmacological driver in a development of a traditional Chinese medicine prescription to treat a disease.

2. The method according to claim 1, wherein the disease-related protein-protein interaction network is composed of ≥100 nodes and ≥200 edges.

3. The method according to claim 2, wherein the disease-related protein-protein interaction network is composed of ≥200 nodes and ≥500 edges.

4. The method according to claim 2, wherein the disease-related protein-protein interaction network is composed of ≥2000 nodes and ≥6000 edges.

5. The method according to claim 1, wherein the at least three first methods utilized in step (3) and the at least three second methods utilized in step (4) are selected from the group consisting of methods of: Degree centrality, Eigenvector centrality, Betweenness centrality, Weighted degree, Stress, and PageRank.

6. The method according to claim 5, wherein the at least three first methods utilized in step (3) are same as the at least three second methods utilized in step (4).

7. The method according to claim 5, wherein the at least three first methods utilized in step (3) are different than the at least three second methods utilized in step (4).

8. The method according to claim 1, wherein the biomolecular network is the disease-related protein-protein interaction network before or after drug intervention.

9. The method of claim 1, wherein the disease is ischemia.

* * * * *